US005700240A

United States Patent [19]
Barwick, Jr. et al.

[11] Patent Number: 5,700,240
[45] Date of Patent: Dec. 23, 1997

[54] PHACOEMULSIFICATION SYSTEM HAVING ULTRASONIC POWER CONTROLLED BY ASPIRATION VACUUM SENSOR

[76] Inventors: Billie John Barwick, Jr., 85 Hull St., Beverly, Mass. 01915; James H. Little, 6601 S. Country Club Dr., Oklahoma City, Okla. 73159

[21] Appl. No.: 378,533

[22] Filed: Jan. 24, 1995

Related U.S. Application Data

[63] Continuation-in-part of Ser. No. 188,188, Jan. 28, 1994, abandoned.

[51] Int. Cl.$^6$ ............................................. A61B 17/20
[52] U.S. Cl. ................. 604/22; 604/65; 604/118; 606/107; 606/159
[58] Field of Search ................. 604/22, 31, 65, 604/67, 118; 601/2; 607/97; 606/159, 107

[56] References Cited

U.S. PATENT DOCUMENTS

| | | | |
|---|---|---|---|
| 3,812,855 | 5/1974 | Banko | 128/276 |
| 4,168,707 | 9/1979 | Douvas et al. | 128/276 |
| 4,425,116 | 1/1984 | Bilstad et al. | 604/34 |
| 4,457,757 | 7/1984 | Molteno | 604/294 |
| 4,475,904 | 10/1984 | Wang | 604/119 |
| 4,479,761 | 10/1984 | Bilstad et al. | 417/395 |
| 4,521,210 | 6/1985 | Wong | 604/8 |
| 4,627,833 | 12/1986 | Cook | 604/34 |
| 4,713,051 | 12/1987 | Steppe et al. | 604/33 |
| 4,735,610 | 4/1988 | Akkas et al. | 604/119 |
| 4,759,238 | 7/1988 | Sundblom et al. | 604/319 |
| 4,798,580 | 1/1989 | DeMeo et al. | 604/30 |
| 4,904,168 | 2/1990 | Cavoto | 417/477 |
| 4,933,843 | 6/1990 | Scheller et al. | 364/413.01 |
| 4,963,131 | 10/1990 | Wortrich | 604/34 |
| 4,966,131 | 10/1990 | Houghton et al. | 128/24 A |
| 4,983,901 | 1/1991 | Lehmer | 318/685 |
| 5,106,366 | 4/1992 | Steppe | 604/30 |
| 5,154,696 | 10/1992 | Shearing | 604/22 |
| 5,230,614 | 7/1993 | Zanger et al. | 417/477 |
| 5,268,624 | 12/1993 | Zanger | 318/551 |
| 5,324,180 | 6/1994 | Zanger | 417/475 |
| 5,342,293 | 8/1994 | Zanger | 604/22 |

FOREIGN PATENT DOCUMENTS

| | | |
|---|---|---|
| 0085518 | 8/1983 | European Pat. Off. . |
| 0293081 | 11/1988 | European Pat. Off. . |
| 0359217 | 3/1990 | European Pat. Off. . |
| 0555625 | 8/1993 | European Pat. Off. . |
| 2076476 | 12/1981 | United Kingdom . |
| 8607249 | 12/1986 | WIPO . |
| WO8607249 | 12/1986 | WIPO . |
| 8705793 | 10/1987 | WIPO . |
| 0362822 | 4/1990 | WIPO . |
| WO9106325 | 5/1991 | WIPO . |
| 9211814 | 7/1992 | WIPO . |

Primary Examiner—Mark Bockelman
Attorney, Agent, or Firm—Walter A. Hackler

[57] ABSTRACT

A method for controlling aspiration and irrigation fluids in an eye during a surgical procedure includes placing a handpiece in an operative relationship with an eye for introducing irrigation fluid and aspiration of fluid from the eye. Irrigation is provided at diverse pressures and aspiration is controlled on the basis of vacuum levels sensed in the handpiece corresponding to an occluded condition of the handpiece. Additionally, during phacoemulsification procedures, ultrasonic power provided to the handpiece may by varied in response to the vacuum levels corresponding to an occluded condition of the handpiece. Apparatus for performing the method of the invention is also provided.

8 Claims, 6 Drawing Sheets

PHACOEMULSIFICATION SYSTEM HAVING ULTRASONIC POWER CONTROLLED BY ASPIRATION VACUUM SENSOR

This application is a continuation-in-part of U.S. patent application Ser. No. 08/188,188, filed on Jan. 28, 1994, and now abandoned.

The present invention is generally directed to a method and apparatus for controlling the flow of fluid from a source to a patient and removal of fluids from the patient through connections with surgical procedures of various types or, more generally, in connection with medical treatments. The flow of fluid to and from a patient through a fluid infusion or extraction system is many times critical to the procedure being performed, such as in ophthalmic microsurgery in which surgical instruments such as electromechanical or pneumatically driven cutters and phacoemulsification instruments are commonly employed. These instruments require a source of fluid to infuse a surgical site and a source of negative pressure to evacuate the infused liquid and debris from the site.

A number of medically recognized techniques has been utilized for lens removal and among these, a popular technique is phacoemulsification, irrigation and aspiration. This method includes the making of a corneal incision, which is typically cauterized to reduce bleeding, and the insertion of a handheld surgical implement which includes a needle which is ultrasonically driven in order to emulsify the eye lens. Simultaneously with this emulsification, a fluid is inserted for irrigation of the emulsified lens and a vacuum provided for aspiration of the emulsified lens and inserted fluids.

The hereinabove described phacoemulsification techniques are well-known in the field of ophthalmology going back to the late 1960s and the work of Dr. Charles Kelman. A full discussion of phacoemulsification is found in Chapter 11, "The Mechanics of Phacoemulsification; Chapter 12, "The Phacoemulsification Procedure"; Chapter 13, "Cataract removal by Phacoemulsification"; and Chapter 14, "Small Pupil Phacoemulsification Techniques of *The Surgical Rehabilitation of Vision—An Integrated Approach to Anterior Segment Surgery*, edited by Lee T. Norman, W. Andrew Maxwell and James A. Davison, Gower Medical Publishing, New York, N.Y., 1992, ISBN 0-397-44693-4. Chapters 11–14 thereof are incorporated herein in their entirety by reference.

Currently available phacoemulsification systems are manufactured and sold by Optical Micro Systems, Inc., of North Andover, Massachusetts, under the trademarks "DIPLOMATE", "DIPLOMATE MMP", "OPSYS" and "OPSYS MMP". These systems have control units that include a variable speed peristaltic pump, a vacuum sensor, an adjustable source of ultrasonic power and a programmable microprocessor with operator-selected presets for controlling aspiration rate, vacuum and ultrasonic power levels.

Many surgical instruments and controls in use today linearly control the vacuum or linearly control the flow of aspiration fluid. This feature allows the surgeon to precisely "dispense" or control the "speed" at which he/she employs, either the vacuum or the flow, but not both. However, there often are times during surgery when the precise control when one of the variables (vacuum, aspiration rate, or ultrasonic power) is desired over the other. The experienced user, understanding the relationship between the vacuum and the flow, may manually adjust the preset variable appropriately at the console in order to obtain an acceptable performance. However, if this adjustment is overlooked, then the combination of both high vacuum and high flow can cause undesirable fluidic surges at the surgical site with possible damage inflicted on the patient.

It should be apparent that the control of hand-held surgical instruments for use in phaco surgery is complex. Phacoemulsifier apparatus typically comprises a cabinet, including a power supply, peristaltic pump, electronic and associated hardware, and a connected, multi-function and handheld surgical implement, or handpiece, including a hollow slender-like needle tube as hereinabove described, in order to perform the phacoemulsification of the cataractous lens.

It should be appreciated that a surgeon utilizing the handheld implement to perform the functions here-in-above described requires easy and accessible control of these functions, as well as the ability to selectively shift or switch between at least some of the functions (for example, irrigation and irrigation plus aspiration) as may arise during phacoemulsification surgery.

In view of the difficulty with adjusting cabinet-mounted controls, while operating an associated hand-held medical implement, control systems have been developed such as described in U.S. Pat. No. 4,983,901. This patent is to be incorporated entirely into the present application, including all specification and drawings for the purpose of providing a background to the complex controls required in phacoemulsification surgery and for describing apparatus which may be utilized or modified for use with the method of the present invention.

To further illustrate the complexity of the control system, reference is also made to U.S. patent application Ser. No. 961,138, filed Oct. 14, 1992, for "Foot Pedal Control with User Selectable Operational Ranges". This patent application is to be incorporated in the present application by this specific reference thereto, including all specifications and drawings for the purpose of further describing the state of the art in the field of this invention.

Further procedures and problems in connection with phacoemulsification, irrigation and aspiration methods and apparatus are discussed in U.S. Pat. No. 5,154,696.

It should thus be apparent, in view of the complex nature of the control system of fluids and ultrasonic power in the case of phacoemulsification procedures, that it is desirable for a surgeon to have a system which is programmable to serve both the needs of the surgical procedure and particular techniques of the surgeon, which may differ depending on the experience and ability of the surgeon.

SUMMARY OF THE INVENTION

In accordance with the present invention, a method is provided for controlling aspiration of fluids from an eye during a surgical procedure, which includes: placing a handpiece in an operational relationship with an eye for aspiration of fluids therefrom; and aspirating fluid from the eye through a handpiece at a selected rate and during aspiration, sensing a vacuum level corresponding to an occluded condition of the handpiece.

The occluded condition restricts aspiration of fluid flow through the handpiece and accordingly, in accordance with the present invention, a selected rate of aspiration through the handpiece is variably controlled in response to the sensed vacuum level.

As this procedure applies to operating a phacoemulsification system, the aspiration rate may be increased in response to an occluded condition of the handpiece or decreased in response to an occluded condition of the handpiece.

Depending upon a physician preference, the aspiration may be increased to accelerate or enhance the removal of the occlusion from the handpiece. This is, of course, dependent upon the characteristics of the material occluding the handpiece. That is, with experience, a physician can more expeditiously remove an occlusion in the handpiece by increasing the aspiration rate. In this manner the physician can control the rate of increase (aspiration rise) of vacuum to a desired vacuum leve. On the other hand, again depending upon the occluding material, the physician may wish to reduce the aspiration rate, for example, to maintain stability of the eye during removal of the occluded material.

In addition, with regard to a method for operating a phacoemulsification system, in accordance with the present invention, ultrasonic power being provided to the handpiece may be variably controlled in response to a sensed vacuum level in the handpiece corresponding to an occluded condition. This control may be increasing the power to the handpiece when an occluded condition is signaled or, alternatively, decreasing the ultrasonic power being provided to the handpiece when an occluded condition is sensed.

Whether the power is increased or decreased depends in part on the technique of the physician and the characteristics of the material, i.e., for example, the hardness of a cataract being removed.

The present invention also encompasses a method for controlling irrigation fluid to an eye during a surgical procedure. In this method, the handpiece is placed in an operative relationship with an eye for introducing irrigation fluid into the eye and aspiration of fluid from the eye, and the handpiece is provided irrigation fluid at a selected pressure.

During aspiration of fluid from the handpiece, a vacuum level corresponding to an occluded condition of the handpiece is sensed, and in response to this sensed vacuum level, irrigation is provided to the handpiece at a different selected pressure.

More particularly, the step of providing irrigation fluid to the handpiece at a selected pressure includes positioning a plurality of irrigation fluid supplies at different heights above the handpiece and fluidly communicating one of the irrigation fluid supplies to the handpiece. The step of providing irrigation fluid to the handpiece at a different selected pressure includes fluidly communicating another of the irrigation fluid supplies to the handpiece while stopping communication of the one irrigation fluid supply to the handpiece.

With regard to phacoemulsification procedures, the present invention encompasses a method for operating a phacoemulsification system, having a phacoemulsification handpiece, an ultrasonic power source, a vacuum source, a source of irrigating fluid, and a control unit having a vacuum sensor for controlling ultrasonic power provided to the handpiece and aspiration of irrigation fluid from the handpiece.

The operating method includes the steps of placing the handpiece in an operative relationship with an eye for phacoemulsification procedures and thereafter supplying irrigation fluid from the irrigation fluid source to and through the handpiece and into the eye. Ultrasonic power is provided from the ultrasonic power source to the handpiece for performing the phacoemulsification procedure, and a vacuum is provided to the handpiece for aspirating irrigation fluid from the eye through the handpiece at a selected rate.

During the fluid aspiration step, a vacuum level in the handpiece corresponding to an occluded condition is sensed, and thereafter, in response to the sensed vacuum level in the handpiece corresponding to the occluded condition of the handpiece, at least one of the provided ultrasonic power and the rate of aspirating irrigation fluid is variably controlled.

Phacoemulsification apparatus, in accordance with the present invention generally includes a handpiece for introducing irrigation fluid to an eye and aspirating fluid from the eye. Means are provided for introducing irrigation fluid to the handpiece at a plurality of pressures and a variable speed pump connected in fluid communication with the handpiece is provided for aspirating, by vacuum, irrigation fluid from the handpiece.

A sensor is connected in fluid communication with the handpiece for sensing vacuum levels in the hand-piece, and a control unit responsive to the sensed vacuum levels in the handpiece is provided for selecting one of the plurality of pressures of irrigation fluid introduced to the handpiece.

More particularly, a phacoemulsification hand-piece may be included, and a power source connected thereto is provided for supplying ultrasonic power to the handpiece. In this instance, the control unit is responsive to the sensed vacuum level in the handpiece for veering at least one of the speed of the pump, the ultrasonic power level provided to the handpiece and the pulse duty cycle of the ultrasonic power provided to the handpiece by the power source.

Means may be provided for introducing irrigation fluid into the handpiece at a plurality of pressures and, in this embodiment, the control unit is responsive to the sensed vacuum levels in the handpiece for selecting one of the plurality of pressures of irrigation fluid introduced into the handpiece.

More specifically, the means for providing an irrigation fluid includes a plurality of containers and a valve interconnected between each of the containers and handpiece. Means are also provided for disposing the containers at different heights over the handpiece when the control unit is connected to the valve, for causing the valve to control fluid communication between each of the containers and the handpiece.

Still more particularly, the phacoemulsification apparatus, in accordance with the present invention, may include a control unit which is responsive to the sensed vacuum levels of the handpiece wherein a pulse duty cycle of the ultrasonic power is provided to the handpiece by the power source. In this instance, the control unit may be connected to the handpiece for first providing an ultrasonic power and first pulse duty cycle until a first predetermined power level of the handpiece is exceeded and thereafter providing ultrasonic power at a second, and greater, pulse duty cycle until a second, and greater, predetermined power level of the handpiece is exceeded. Optionally, thereafter, ultrasonic power may be provided to a third, and still greater, pulse duty cycle until a third, and still greater, predetermined power level of the handpiece is exceeded, and thereafter providing power at a pulse duty cycle greater than the third duty cycle.

BRIEF DESCRIPTION OF THE DRAWINGS

The advantages and features of the present invention will be better understood by the following description when considered in conjunction with the accompanying drawings in which.

DETAILED DESCRIPTION OF THE INVENTION

Figure 1:
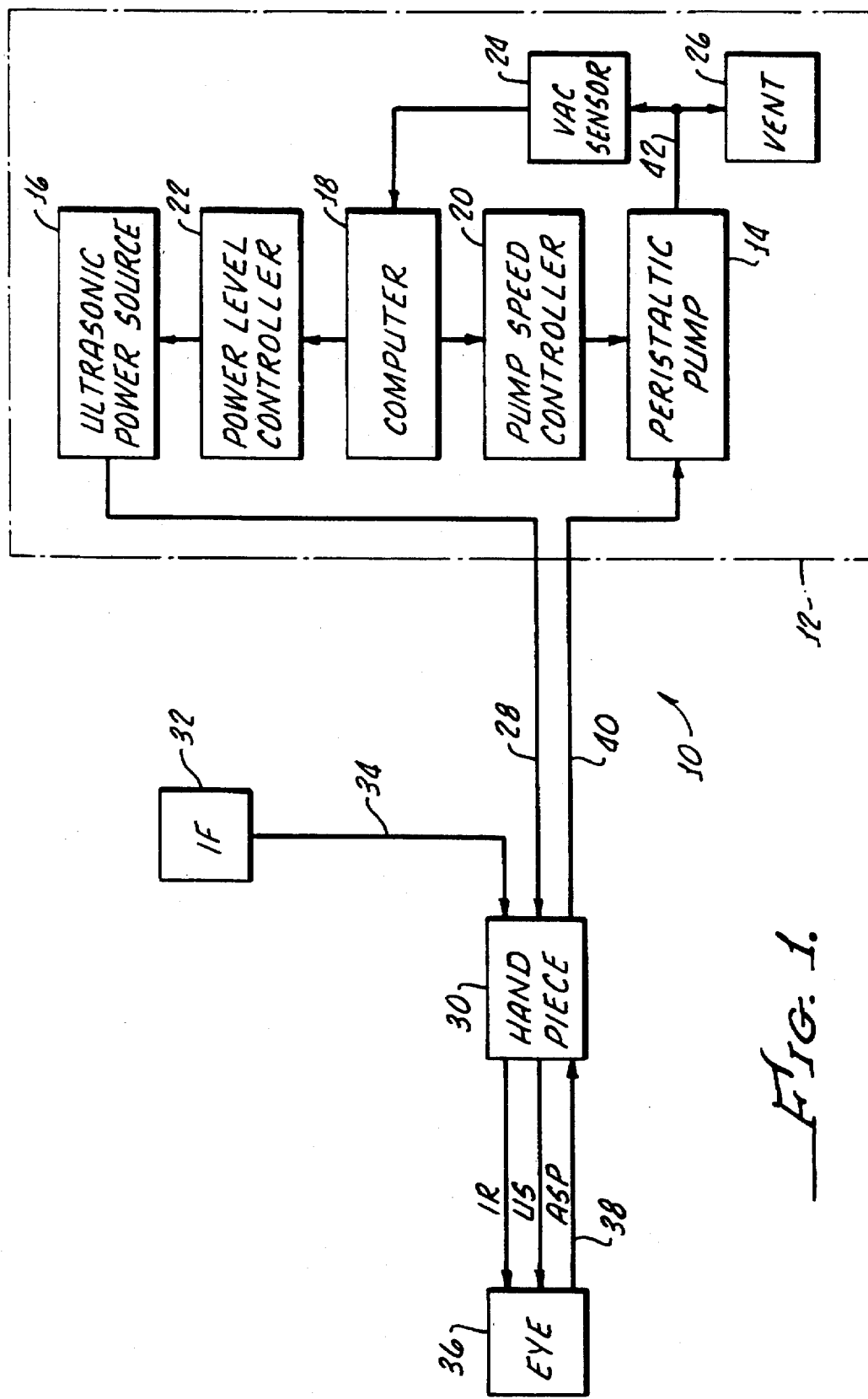
FIG. 1 is a functional block diagram of a phacoemulsification system in accordance with the present invention.

Turning now to the drawings, and particularly to FIG. 1 thereof, there is shown, in functional block diagram form, a phacoemulsification system indicated generally by the reference numeral 10. The system has a control unit 12, indicated by the dashed lines in FIG. 1 which includes a variable speed peristaltic pump 14, which provides a vacuum source, a source of pulsed ultrasonic power 16, and a microprocessor computer 18 that provides control outputs to pump speed controller 20 and ultrasonic power level controller 22. A vacuum sensor 24 provides an input to computer 18 representing the vacuum level on the output side of peristaltic pump 14. Suitable venting is provided by vent 26.

The components of the system 10 are available from various sources. For example, the power source 16 is available from ALCON (Series 10000) as is the power level controller (also Series 10000). The computer 18 may an NEC 8085 and the pump speed controller 20 may be a Pittman GM9434H777. The vacuum sensor 24 may be a Sensym SCX100DN and the vent 26 may be an LDI model 11-12-3-BV -24 .

The control unit 12 supplies ultrasonic power on line 28 to a phacoemulsification handpiece 30. (Which may be an ALCON model 590-2000-501.) An irrigation fluid source 32 (Which may be an ALCON model 10000) is fluidly coupled to handpiece 30 through line 34. The irrigation fluid and ultrasonic power are applied by handpiece 30 to a patient's eye which is indicated diagrammatically by block 36. Aspiration of the eye 36 is achieved by means of the control unit peristaltic pump 14 through lines 38 and 40.

The computer 18 responds to preset vacuum levels in output line 42 from peristaltic pump 14 by means of signals from the previously mentioned vacuum sensor 24. Operation of the control unit in response to the occluded-unoccluded condition of handpiece 30 is shown in the flow diagram of FIG. 2.

Figure 2:
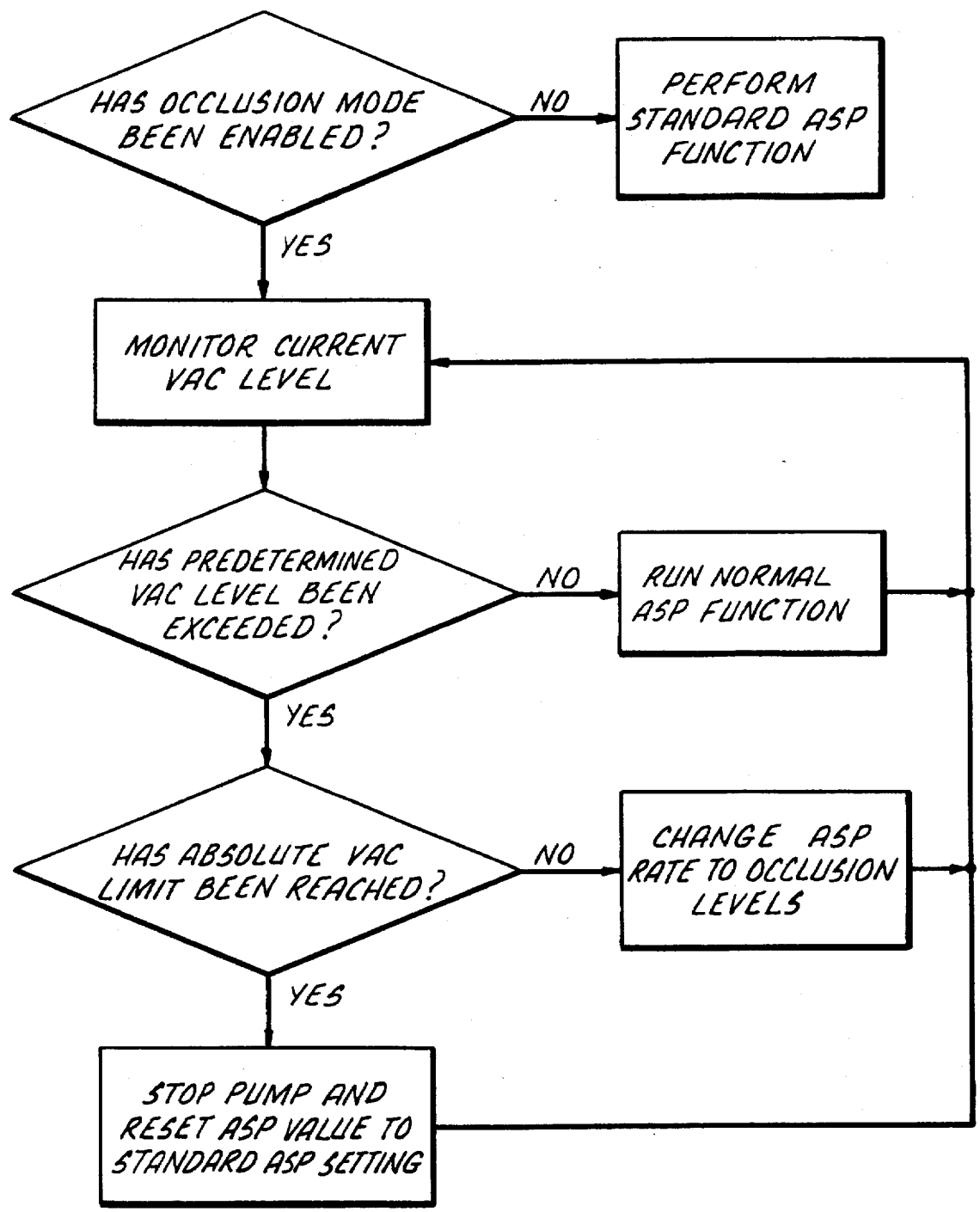
FIG. 2 is a flow chart illustrating the operation of the occluded-occluded mode of the phacoemulsification system with variable aspiration rates.

As shown in FIG. 2, if the handpiece aspiration line 38 is occluded, the vacuum level sensed by vacuum sensor 24 will increase. The computer 18 has operator-settable limits for aspiration rates, vacuum levels and ultrasonic power levels. As illustrated in FIG. 2, when the vacuum level sensed by vacuum sensor 24 reaches a predetermined level as a result of occlusion of the handpiece aspiration line 38, computer 18 instructs pump speed controller 20 to change the speed of the peristaltic pump 14 which, in turn, changes the aspiration rate. It will be appreciated that depending upon the characteristics of the material occluding handpiece 30, the speed of the peristaltic pump 14 can either be increased or decreased. When the occluding material is broken up, the vacuum sensor 24 registers a drop in vacuum level, causing computer 18 to change the speed of peristaltic pump 14 to an unoccluded operating speed.

Figure 3:
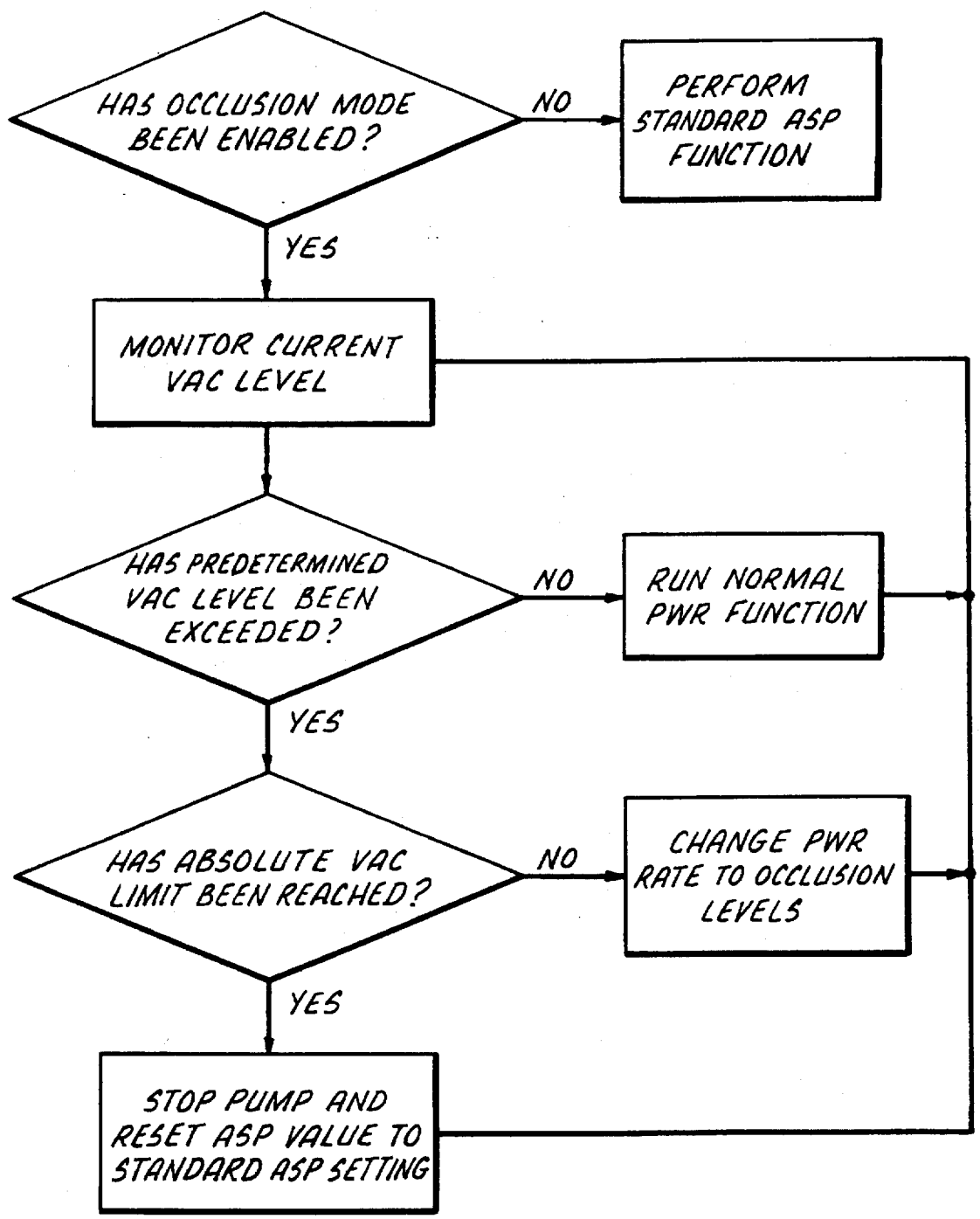
FIG. 3 is a flow chart illustrating the operation of the occluded-occluded mode of the phacoemulsification system with variable ultrasonic power levels.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 3 illustrates in flow diagram form the control of the ultrasonic power source power level by means of computer 18 and power level controller 22. It will be appreciated that the flow diagram of FIG. 3 corresponds to the flow diagram of FIG. 2 but varies the phacoemulsification parameter of the ultrasonic power level.

Figure 4:
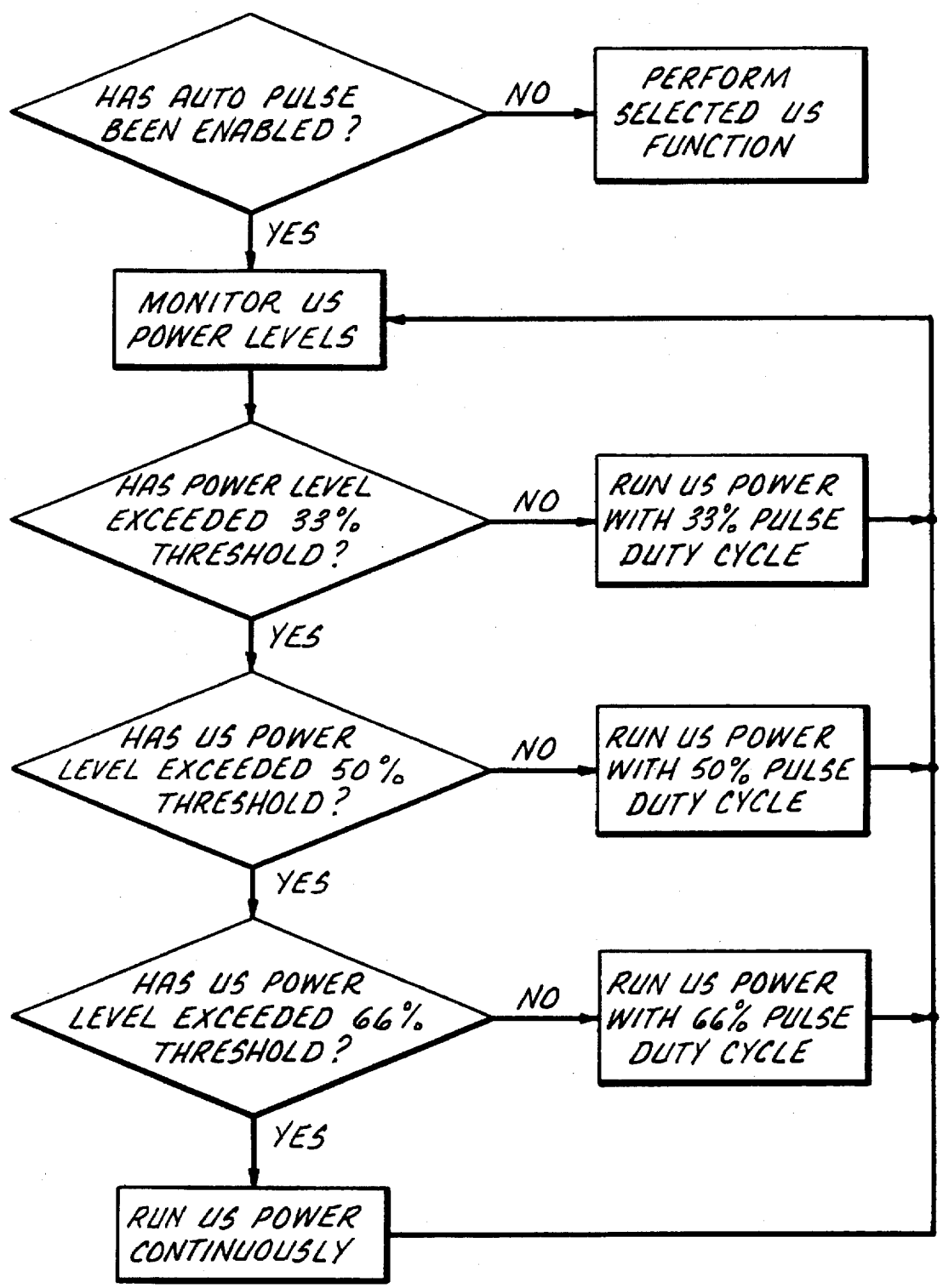
FIG. 4 is a flow chart illustrating the operation of the variable duty cycle pulse function of the phacoemulsification system.

With reference to FIG. 4, there is shown a flow diagram depicting the control of the ultrasonic power source 16 to produce varying pulse duty cycles as a function of selected power levels. As shown in FIG. 4, and by way of illustration only, a 33% pulse duty cycle is run until the power level exceeds a preset threshold; in this case, 33%. At that point, the pulse duty cycle is increased to 50% until the ultrasonic power level exceeds a 50% threshold, at which point the pulse duty cycle is increased to 66%. When the ultrasonic power level exceeds 66% threshold, the power source is run continuously, i.e., a 100% duty cycle. Although the percentages of 33, 50 and 66 have been illustrated in FIG. 4, it should be understood that other percentage levels can be selected to define different duty cycle shift points.

Figure 1A:
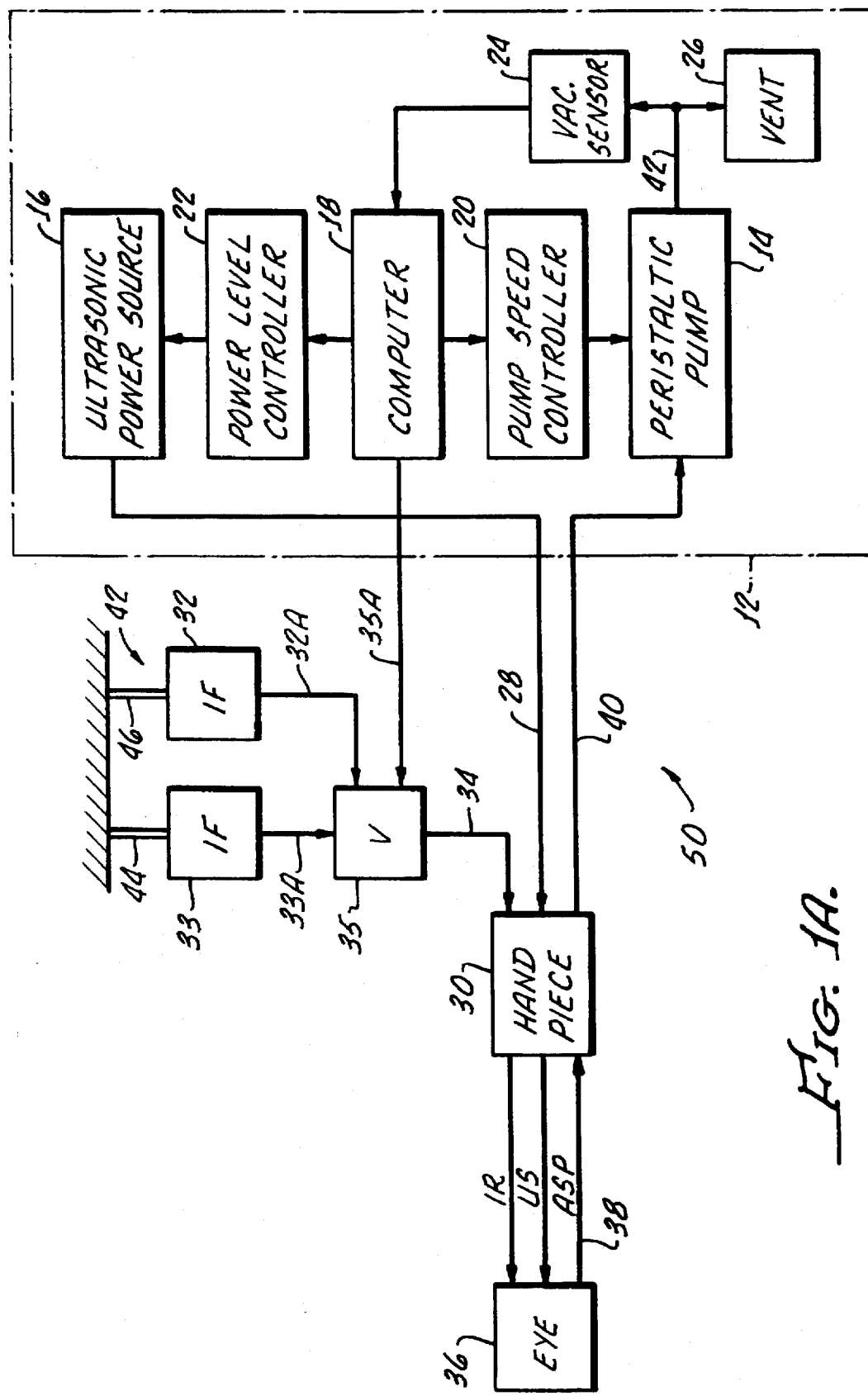
FIG. 1A is a functional block diagram of an alternative embodiment of a phacoemulsification system in accordance with the present invention which includes apparatus for providing irrigation fluid at more than one pressure to a handpiece.

Turning back to FIG. 1A, there is shown an alternative embodiment 50 of a phacoemulsification system, in accordance with the present invention, and which incorporates all of the elements of the system 10 shown in FIG. 1, with identical reference characters identifying components, as shown in FIG. 1.

In addition to the irrigation fluid source 32, a second irrigation fluid source 33 is provided with the sources 32, 33 being connected to the line 34 entering the handpiece 30 through lines 32a, 33a, respectively, and to a valve 35. The valve 35 functions to alternatively connect line 32a and source 32 and line 33a and source 33 with the handpiece 30 in response to a signal from the power level controller 22 through a line 35a.

As shown, irrigation fluid sources 32, 33 are disposed at different heights above the handpiece, providing a means for introducing irrigation fluid to the handpiece at a plurality of pressures, the head of the fluid in the container 33 being greater than the head of fluid in the container 32. A harness 42, including lines of different lengths 44, 46, when connected to the support 48, provides a means for disposing the containers 32, 33 at different heights over the handpiece 30.

The use of containers for irrigation fluids at the various heights is representative of the means for providing irrigation fluids at different pressures, and alternatively, separate pumps may be provided with, for example, separate circulation loops (not shown) which also can provide irrigation fluid at discrete pressures to the handpiece 30 upon a command from the power controller 22.

Figure 5:
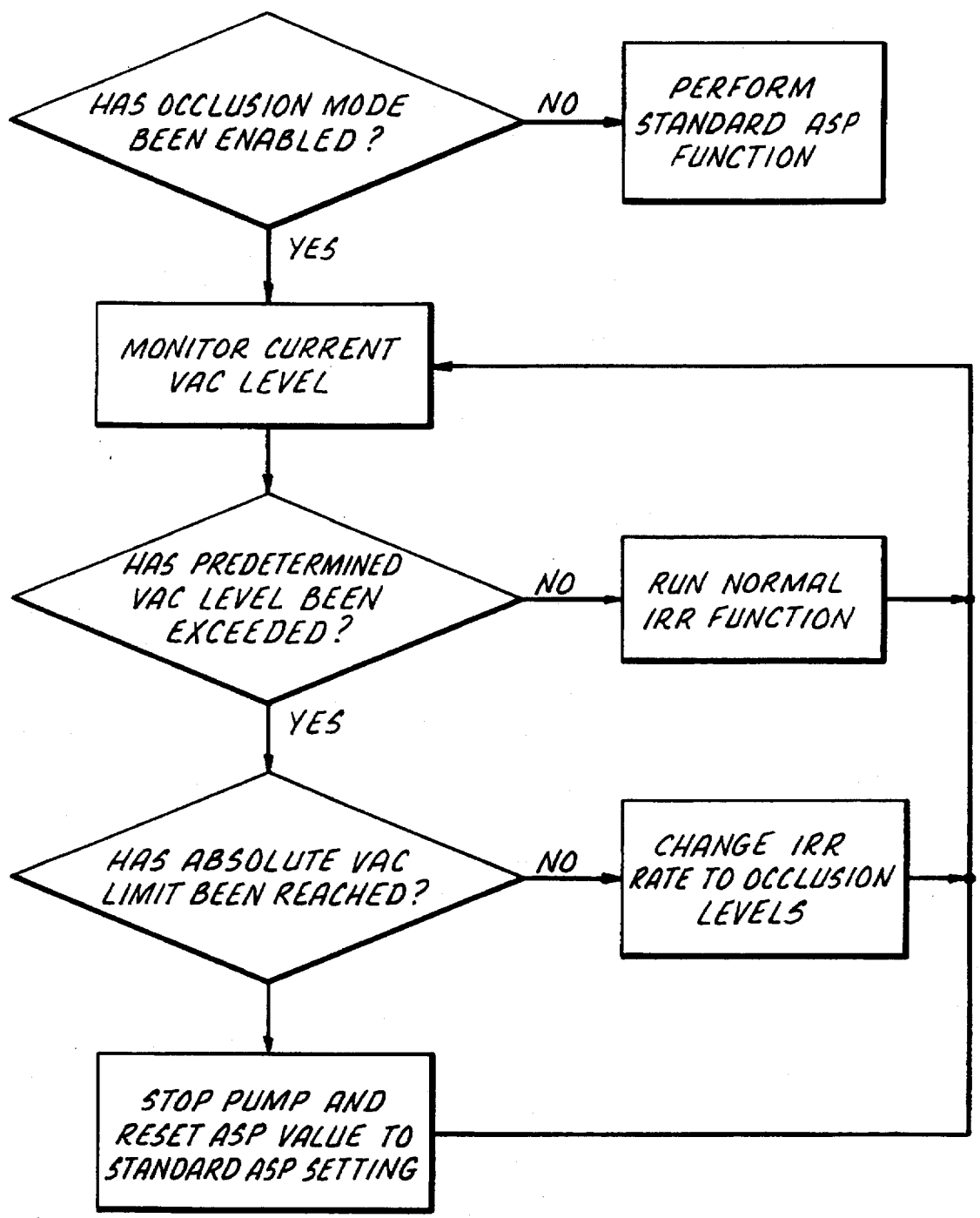
FIG. 5 is a flow chart illustrating the operation of the occluded-unoccluded mode of the phacoemulsification system with variable irrigation rates.

With reference to FIG. 5, if the handpiece aspiration line 38 is occluded, the vacuum level sensed by the vacuum sensor 24 will increase. The computer 18 has operator-settable limits for controlling which of the irrigation fluid supplies 32, 33 will be connected to the handpiece 30. It should be appreciated that while two irrigation fluid sources, or containers 32, 33, are shown, any number of containers may be utilized.

As shown in FIG. 5, when the vacuum level by the vacuum sensor 24 reaches a predetermined level, as a result of occlusion of the aspiration handpiece line 38, the computer controls the valve 35 causing the valve to control fluid communication between each of the containers 32, 33 and the handpiece 30. It should be appreciated that, depending upon the characteristics of the material occluding the handpiece 30 as hereinabove described and the needs and techniques of the physician, the pressure of irrigation fluid provided the handpiece may be increased or decreased. As occluded material 24, the vacuum sensor 24 registers a drop in the vacuum level causing the valve 35 to switch to a container 32, 33, providing pressure at an unoccluded level. As noted hereinabove, it should be appreciated that more than one container may be utilized in the present invention, as an additional example, three containers (not shown) with the valve interconnecting to select irrigation fluid from any of the three containers, as hereinabove described in connection with the FIG. 1A container system.

Although there has been hereinabove described a method for controlling aspiration of fluids, a method for controlling irrigation fluid, and a method for operating a phacoemulsification, as well as phacoemulsification apparatus, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for operating a phacoemulsification system, the system including a phacoemulsification handpiece, an ultrasonic power source, a vacuum source, a source of irrigating fluid, and a control unit having a vacuum sensor for controlling ultrasonic power provided to the handpiece and the aspiration of irrigating fluid from the handpiece, said operating method comprising the steps of:

(a) placing the handpiece in an operative relationship with an eye for a phacoemulsification procedure;

(b) supplying irrigation fluid from the irrigation fluid source to and through the handpiece and into said eye;

(c) providing ultrasonic power from the ultrasonic power source to the handpiece for performing the phacoemulsification procedure;

(d) applying vacuum from the vacuum source to the handpiece and thereby aspirating the irrigating fluid from the eye through the handpiece at a selected rate;

(e) during said fluid aspiration step, sensing a vacuum level in the handpiece corresponding to an occluded condition of the handpiece; and (f) variably controlling, in response to a sensed vacuum level in the handpiece corresponding to the occluded condition of the handpiece, the ultrasonic power being provided to the handpiece.

2. The operating method as claimed in claim 1, wherein the variably controlling step comprises increasing the ultrasonic power being provided to the handpiece, in response to the sensed vacuum level in the handpiece, corresponding to the occluded condition of the handpiece.

3. The operating method as claimed in claim 1, wherein the variably controlling step comprises decreasing the ultrasonic power being provided to the handpiece, in response to the sensed vacuum level in the handpiece, corresponding to the occluded condition of the handpiece.

4. The operating method as claimed in claim 1, wherein the step of providing ultrasonic power to the handpiece comprises the sequential steps of:

(a) providing ultrasonic power at a first pulse duty cycle until a first predetermined power level in the handpiece is exceeded;

(b) providing ultrasonic power at a second, and greater, pulse duty cycle until a second, and greater, predetermined power level in the handpiece is exceeded;

(c) providing ultrasonic power at a third, and still greater, pulse duty cycle until a third, and still greater, predetermined power level in the handpiece is exceeded; and (d) thereafter providing ultrasonic power at a pulse duty cycle greater than said third duty cycle.

5. Phacoemulsification apparatus which comprises:

a phacoemulsification handpiece;

means for providing irrigation fluid to the handpiece;

a variable speed pump connected in fluid communication with said handpiece for aspirating, by vacuum, irrigation fluid from said handpiece;

a power source connected for providing ultrasonic power to said handpiece;

a sensor connected in fluid communication with said handpiece for sending vacuum levels in said handpiece; an a control unit, responsive to the sensed vacuum levels in said handpiece, for varying the ultrasonic power level provided to said handpiece by said power source.

6. The phacoemulsification apparatus as claimed in claim 5, wherein said control unit is responsive to the sensed vacuum levels in said handpiece for varying a pulse duty cycle of the ultrasonic power provided to said handpiece by the power source.

7. The phacoemulsification apparatus as claimed in claim 5, wherein said control unit comprises:

(a) means for providing ultrasonic power at a first pulse duty cycle until a first predetermined power level in the handpiece is exceeded;

(b) means for providing ultrasonic power at a second, and greater, pulse duty cycle until a second, and greater, predetermined power level ill the handpiece is exceeded;

(c) means for providing ultrasonic power at a third, and still greater, pulse duty cycle until a third, and still greater, predetermined power level in the handpiece is exceeded; and (d) means for providing ultrasonic power at a pulse duty cycle greater than said third duty cycle.

8. The phacoemulsification apparatus as claimed in claim 5, wherein the means of providing irrigation fluid to the handpiece comprises a plurality of irrigation fluid supplies disposed at different heights above the phacoemulsification handpiece and valve means for selectively fluidly connecting one of the irrigation fluid supplies to the phacoemulsification handpiece, said valve means being controlled by said control unit, and said control unit being responsive to the sensed vacuum level in the handpiece for causing the valve means to selectively fluidly connect one of the irrigation fluid supplies to the handpiece.

* * * * *